United States Patent
Potter

(10) Patent No.: US 6,521,451 B2
(45) Date of Patent: Feb. 18, 2003

(54) SEALED CULTURE CHAMBER

(75) Inventor: Steve M. Potter, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/733,644

(22) Filed: Dec. 8, 2000

(65) Prior Publication Data
US 2001/0024821 A1 Sep. 27, 2001

Related U.S. Application Data
(60) Provisional application No. 60/170,075, filed on Dec. 9, 1999.

(51) Int. Cl.[7] ................................................. C12N 5/00
(52) U.S. Cl. ..................... 435/383; 435/371; 435/286.6; 435/297.5; 435/303.1; 435/305.4; 435/285.2
(58) Field of Search .......................... 435/41, 325, 371, 435/383, 286.6, 297.1, 297.5, 303.1, 305.4, 285.2

(56) References Cited

U.S. PATENT DOCUMENTS

| | | | | |
|---|---|---|---|---|
| 3,941,662 A | * | 3/1976 | Munder et al. | |
| 3,948,732 A | * | 4/1976 | Hadad et al. | |
| 5,817,509 A | * | 10/1998 | Stevens et al. | 435/297.5 |
| 5,858,770 A | | 1/1999 | Perlman | 435/305.3 |
| 5,863,792 A | * | 1/1999 | Tyndorf et al. | 435/297.5 |

OTHER PUBLICATIONS

Barbera–Guillem, Emilio, "OptiCell (tm)—building block for in vitro pharmacokinetic and pharmacodynamic studies", Innovations in Pharmaceutical Technology, Innovation Feature, pp. 50 and 51.

Barbera–Guillem, Emilio and Swartz, John M., "OptiCell Concept for Cell Culture Operations: Novel Technology for Cell Growth and Monitoring", Genetic Engineering, Dec. 2000, 4 pages, vol. 20., No. 21, Daily Biotech Updates.

Barbera–Guillem, Emilio, "Overcoming cell culture barriers to meet the demands of cell biology and biotechnology", American Biotechnology Laboratory, May 2001, 3 pages.

Glaser, Vicki, "Current Trends and Innovations in Cell Culture: Hybridomas, Stem Cells, Serum–free Media, and Contract Production", Genetic Engineering, Jun. 1, 2001, 6 pages, vol. 21, No. 11, Daily Biotech Updates.

Internet Papers, OptiCell is Total Cell Management Opticell, http://www.opticell.com/products/opticell.html, 2 pages.

Pramik, Mike, "Necessity inspires successor to petri dish", www.opticell.com, Jun. 7, 2001, 2 pages.

Gross, G.W. and Kowalski, J.; "Neural Networks: Concepts, applications and implementations"; P. Antognetti and E.B. Militinovic, eds., N.J. Prentice–Hall, vol. 4, pp. 47–110.

Gross, G.W. and Schwalm, F.U.; "A closed flow chamber for long–term multichannel recording and optical monitoring"; Journal of Nueroscience Methods; vol. 52; pp. 73–85; 1994.

Freyberg, M.A. and Friedl, P.; The use of a conventional tissue culture plate as an optically accessible perfusion chamber for in situ assays and for long–term cultivation of mammalian cells; Cytotechnology; vol. 26; pp. 49–58; 1998.

(List continued on next page.)

Primary Examiner—David A. Redding
(74) Attorney, Agent, or Firm—Christie, Parker & Hale, LLP

(57) ABSTRACT

A gas permeable cover for a cell culture or medium storing container which comprises a solid support sized to fit the opening of the container to be covered and has at least one hole which is covered with a permeable section. The permeable section is sufficiently permeable to oxygen and carbon dioxide that live cells can be sustained, and is substantially impermeable to water and water vapor such that the covered containers can be stored in non-humidified chambers without substantial evaporation of water. The cover further has a seal portion which forms a water-and gas-tight seal between the cover and the container when the cover is placed upon the container as configured for use.

41 Claims, 3 Drawing Sheets

OTHER PUBLICATIONS

"Society for Neuroscience"; Abstracts; vol. 21, part 1; 25th Annual Meeting; San Diego, California; Nov. 11–16, 1995; 2 pp.

Welsh, David K., Logothetis, Diomedes E., Meister, Markus and Reppert, Steven M.; "Individual Neurons Dissociated from Rat Suprachiasmatic Nucleus Express Independently Phased Circadian Firing Rhythms"; Neuron, vol. 14, PP. 697–706; Apr., 1995.

Spierenberg, G.T., Oerlemans, F.T.J.J., Van Laarhoven, J.P.R.M. and Bruyn C.H.M.M; "Phototoxicity of N–2–Hydroxyethylpiperazine–N'–2–3thanesulfonic Acid–buffered Culture Media for Human Leukemic Cell Lines"; Cancer Research; vol. 44, pp. 2253–2254; May 1984.

Lepe–Zuniga, Jose Luis, Zigler, J.S., Jr. and Gery, Igal; "Toxicity of light–exposed Hepes media"; Journal of Immunological Methods; vol. 103; p. 145; 1987.

Kiehart, et al, "High–Resolution Microscopic Methods for the Analysis of Cellular Movements in Drosophila Embryos," Methods in Cell Biology, vol. 44, Ch. 26, 1994, pp. 507–532.

Lowe, et al, "Perfluorochemicals and Cell Biotechnology," Art, Cells, Blood Subs., And Immob. Biotech., 25(3), 1997, pp. 261–274.

* cited by examiner

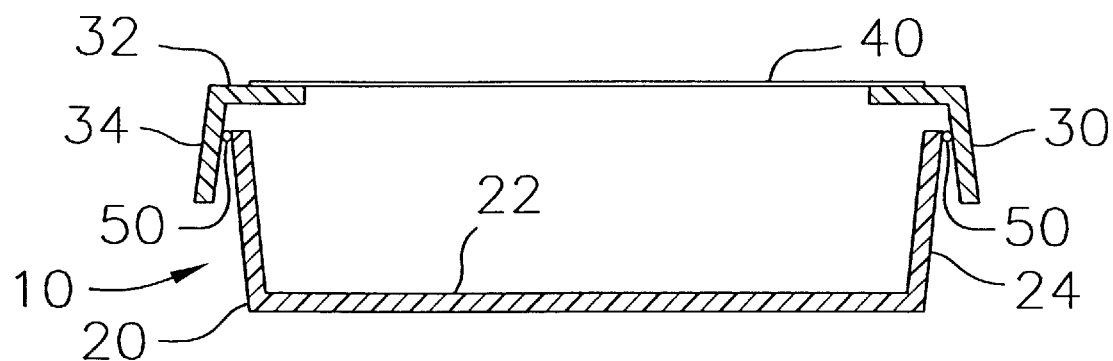
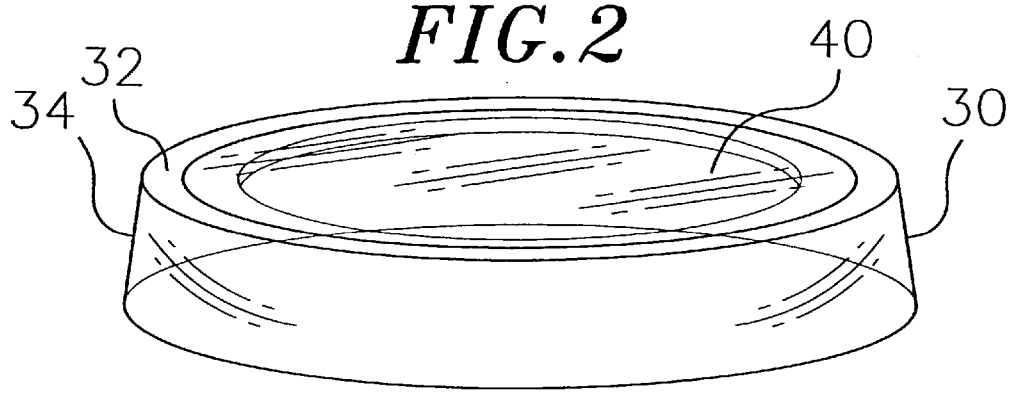
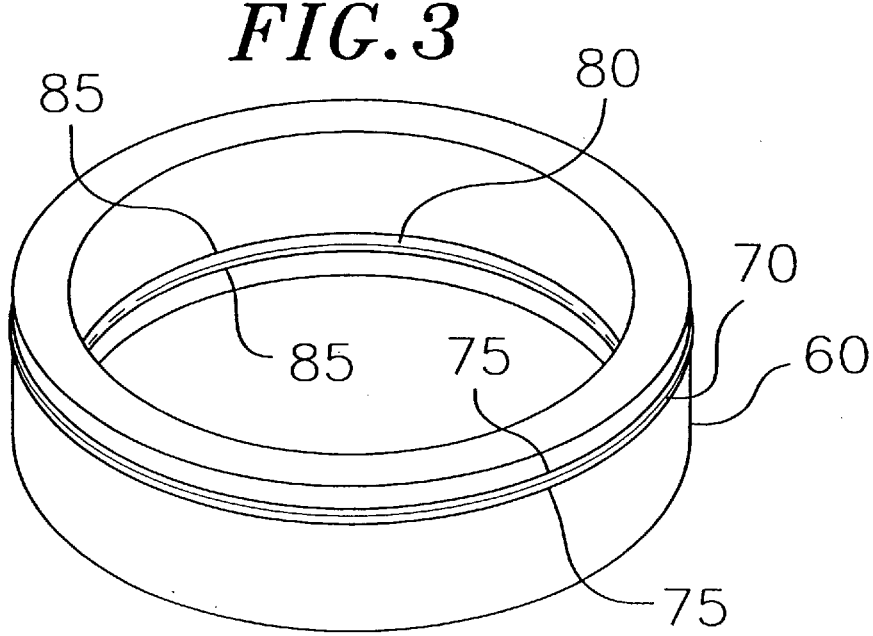

SEALED CULTURE CHAMBER

CROSS-REFERENCE TO RELATED APPLICATION(S)

This application claims priority of U.S. Provisional Application No. 60/170,075, filed Dec. 9, 1999, the disclosure of which is herein incorporated by reference.

STATEMENT REGARDING FEDERALLY SPONSORED RESEARCH OR DEVELOPMENT

This invention was made in part with government support under Grant No. R01-NS38628 awarded by the National Institute of Neurological Disorders and Stroke. The government therefore has certain rights in the invention.

BACKGROUND OF THE INVENTION

Cell culture techniques have long been established for particular cell and tissue types and uses, and continuation of cell viability depends on many factors. One common problem is contamination of cultures in the incubator by airborne contaminants such as mold spores and opportunistic bacteria. The problem lies in the incubator conditions; incubators are generally humidified to close to 100% in order to inhibit evaporation of water from the culture media within the culture dishes. The standard solution to this problem is decontamination of the incubator, a time-consuming task and difficult or impossible to do completely. There is no guarantee that a recently cleaned incubator will remain mold-free for long, especially if already-infected cultures are returned to it. The warm, humid environment found in mammalian and bacterial cell incubators is ideal for the proliferation of mold and bacteria.

The use of completely sealed culture dishes to prevent evaporation of the water in culture media is not possible in the culture of cells, because a transport of gasses to and from the culture chamber is necessary to ensure cell viability. Cells consume oxygen and produce carbon dioxide, and these gasses must be maintained in the culture space within certain levels to prevent pH changes in the medium and provide adequate oxygen for cellular metabolism. To maintain physiological pH around 7.3, most culture media use a buffering system in which there is an equilibrium between dissolved $CO_2$ (bicarbonate anion) and a well-regulated 5% (v/v) $CO_2$ atmosphere in the incubator. When brought into room atmosphere (less than about 0.1% $CO_2$), bicarbonate leaves the medium as gaseous $CO_2$ and the pH drifts up to over 8.5. Some media designed for ambient $CO_2$ levels (such as Hibernate, Life Technologies, Inc., Gaithersburg Md.) use additional buffers, such as MOPS or HEPES, to maintain proper pH. However, HEPES and other synthetic organic buffers maybe highly phototoxic, even under standard fluorescent ceiling lights (Spierenburg, G. T. et al. (1984), *Cancer Research* 44(5):2253–2254; Lepe-Zuniga, J. L., et al. (1987), *Journal of immunological Methods* 103(1): 145–145).

A need exists for a cell culture system that reduces the risk of contamination, but prevents evaporation of water from cultures and supplies cells with the gasses necessary for viability.

SUMMARY OF THE INVENTION

A system for culturing cells has been developed that eliminates the problem of infection from the incubator and prevents water loss from evaporation of medium, yet permits the exchange of necessary gasses. The container covers and culture dishes of the invention have permitted culture of cells for prolonged periods, longer than the standard culture time of about 2 weeks, up to 12 months or longer.

In one embodiment, the invention includes a gas permeable cover for a container, which comprises a solid support sized to fit the opening of the container to be covered. The support has at least one hole which is covered by a permeable section, preferably a membrane, which is sufficiently permeable to oxygen and carbon dioxide that cultures of live cells can be sustained. The permeable section is substantially impermeable to water and water vapor. "Substantially impermeable to water" as used herein means that water and water vapor passes across the permeable section at a rate less than about 5 mol/m²·day at 25° C. and 1 atmosphere. Finally, the cover has a seal portion which forms a water- and gas-tight seal between the cover and the container when the cover is placed upon or engages the container as configured for use.

Preferably, the gas permeable section of the cover passes water and water vapor at a rate of less than about 3 mol/m²·day, more preferably less than about 2 mol/m²·day, most preferably less than about 1 mol/m²·day at 25° C. and 1 atmosphere. The permeable section preferably passes oxygen gas at a rate of greater than about 0.25 mol/m²·day, more preferably at a rate of greater than about 0.5 mol/m²·day, and most preferably at a rate of greater than about 0.8 mol/m²·day at 25° C. and 1 atmosphere. It preferably also passes carbon dioxide gas at a rate of greater than about 0.5 mol/m²·day, more preferably greater than about 1.0 mol/m²·day, and most preferably greater than about 1.5 mol/m²·day at 25° C. and 1 atmosphere. These parameters provide the advantage that the cell culture does not dry out over time and thus does not have to be maintained in a humidified incubator. Because humidified incubators often harbor contaminating microorganisms, the ability to culture cells in a reduced humidity incubator reduces the growth of such microorganisms, and thus also reduces risk of contamination of the culture by opportunistic microorganisms.

In another embodiment, the invention includes a culture dish for the culture of viable cells comprising a culture portion having a bottom part and elevated walls surrounding the bottom part, the culture portion being capable of containing the cells, and a lid portion having a permeable section, the permeable section being sufficiently permeable to oxygen and carbon dioxide that viable cells can be sustained, and substantially impermeable to water and water vapor. The lid portion has a seal region which can form a seal that is both water-tight and gas-tight between the culture portion and the walls of the culture portion when the two are configured for use. Preferably, the water- and gas-tight seal is a friction seal, created by e.g., the weight of the lid portion against the walls of the culture dish or a gasket or other material sufficiently elastic/flexible to conform to the walls.

In preferred embodiments, the permeable section is fixedly attached onto the lid portion, such as by glue, thermal, or ultrasonic bonding. Alternatively, the lid portion, or the entire vessel, can be made of substantially entirely the same material as the permeable section. The permeable section is preferably comprised of an optically clear and flat membrane, preferably a fluorinated ethylene-propylene film. This allows for imaging or surveillance of the culture without removing the cover, reducing the risk of contamination, evaporation, and pH changes. Preferably, the permeable section is impermeable to viruses, mold, bacteria, and fungi.

In other embodiments, the dish further comprises at least one electrode, more preferably an array of electrodes. In still other embodiments, the dish further comprises at least one infusion and/or outflow pipe or port for changing medium or infusing drugs, for example.

The invention also features a method of culturing cells comprising providing cells and culture medium in a culture vessel, where the culture vessel comprises a culture container portion capable of containing the cells and a cover portion. The cover portion has a solid support sized to fit the opening of the container and has at least one hole which is covered by a permeable section that is sufficiently permeable to oxygen and carbon dioxide so that live cells can be sustained. It is also substantially impermeable to water and water vapor. The cover also has a seal portion which forms a water- and gas-tight seal between the cover and the container when the cover is placed on the container as configured for use. The method includes incubating the cells under conditions physiologically compatible with cell viability. Cells can be maintained for long periods with this method by periodically changing a sufficient amount of the culture medium such that the cells have sufficient nutrients and toxic levels of waste are removed, because evaporation of the medium is greatly reduced. The relative impermeability also allows the cells to be incubated in an incubator that is not humidified, but rather kept at ambient relative humidity.

BRIEF DESCRIPTION OF THE DRAWINGS

FIG. 1 is a vertical cross-sectional view of a single well culture chamber constructed according to the invention.

FIG. 2 is a perspective view of a cover for a culture chamber constructed according to another embodiment of the invention.

FIG. 3 is a perspective view of yet another embodiment of the cover portion of the invention, having o-rings to secure the permeable portion and form the water- and gas-tight seal with the vessel.

FIG. 6a is a top view of a single well culture chamber including an electrode array comprising a plurality of electrodes according to the current invention.

FIG. 6b is a side view of a single well culture chamber including an electrode according to the current invention.

FIG. 7 is a side view of a single well culture chamber including an infusion and outflow port according to the current invention.

DETAILED DESCRIPTION OF THE INVENTION

Figure 4:
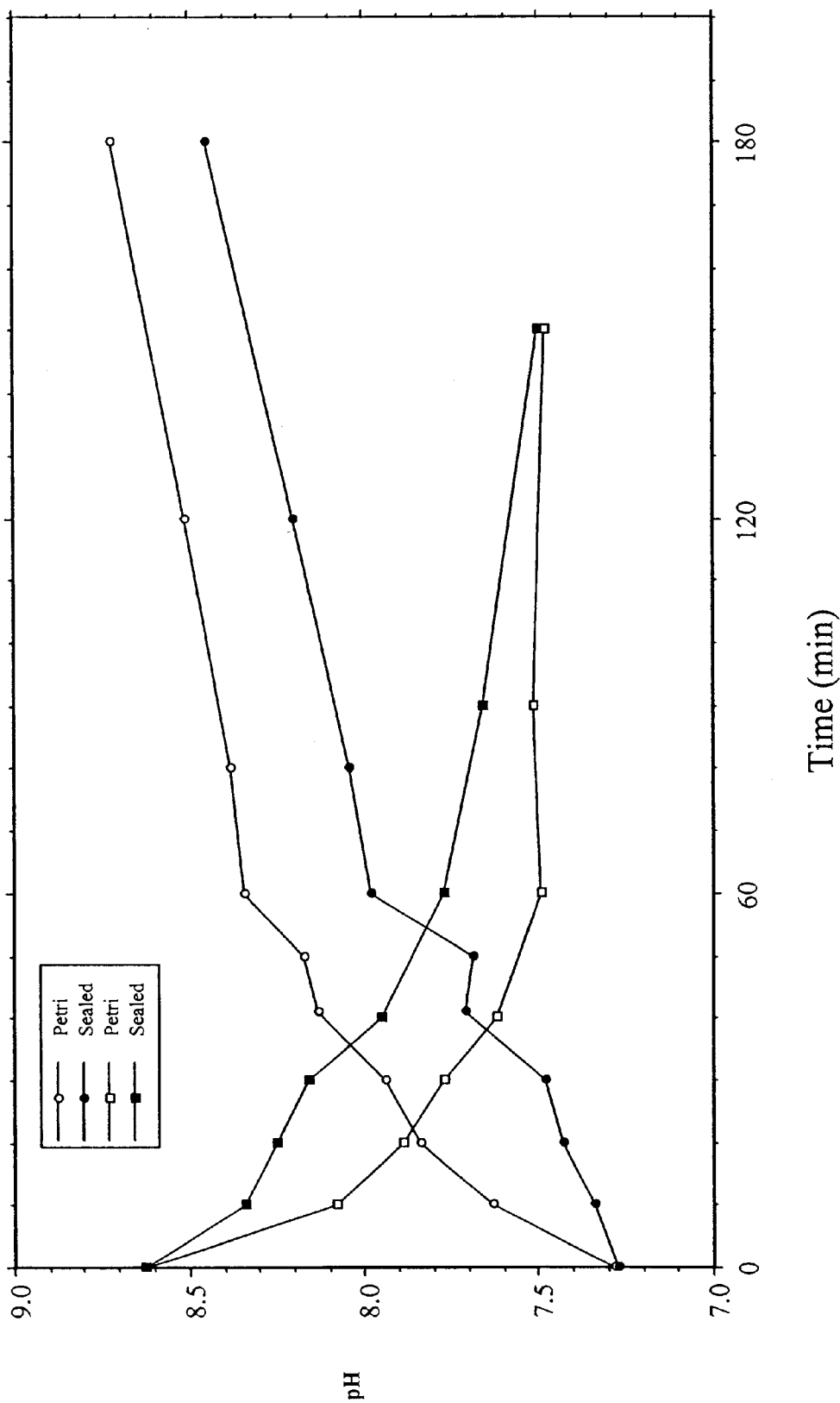
FIG. 4 is a graph showing Change in osmolarity of culture medium due to evaporation of water. Each dish (containing standard MEM with 10% horse serum, and no cells) was measured only once and discarded, and all time points are averages of duplicates. Mean conditions in laminar flow hood during measurement period, 26° C., 59% R.H. Least-squares linear regression gives daily osmolarity increases of 58.6 mOsm for normal dishes in the laminar flow hood (open circles), 10.5 mOsm for normal dishes in the humidified incubator (open squares), and 4.0 mOsm for the FEP-sealed dishes in the dry incubator (filled triangles).

The cell culture apparatus and methods of the invention permit cells, tissues, organs, embryos, etc., to be cultured using standard media and growth conditions, but alleviate the need for certain environmental conditions such as humidity control. Furthermore, cells can be maintained for much longer periods of time than they can be using standard culture materials and conditions. Using the cell culture dish and covers of the invention, a non-humidified incubator can be used, reducing the contamination that often results from storage in high relative humidity incubators, evaporation of the water in culture media with its attendant osmolarity problems is avoided, and the cells can be studied in the culture dish in the same manner as when cells are cultured in standard culture dishes and incubators.

Culture dishes of the invention are sealed with a selectively-permeable membrane, and need not be maintained in a humidified incubator. This system was developed in order to allow repeated recording from primary neural cultures growing on multi-electrode array dishes, but has wide applicability to most cell culture systems.

The invention features a container or a cover therefor, for example a culture dish, flask, vivarium, or the like, which is suitable for the maintenance or culture of any cell, tissue, organ, embryo, or organism that may be desired, or the storage of culture media or other solutions or reagents, for example those that are best equilibrated with a particular environment before use. The container has a portion suitable for holding the cells to be cultured or other product, and a portion that serves as a lid or cover. The lid portion has at least a subsection that is composed of a material permeable to gases such as carbon dioxide and oxygen, but is, relatively speaking, substantially impermeable to water, even in its gaseous vapor form. Some embodiments include just lids, covers, or closure portions for existing flasks, bottles, or other containers. Such lids or containers permit, for example, equilibration of media before changing the cell culture medium (to prevent pH or temperature shock), growth of cells in other than a culture dish (e.g., a suspension culture), etc.

In a preferred embodiment, shown in FIG. 1, the container is a culture dish 10, and is designed to culture and maintain viable cells. It can be of any size, shape, or configuration to accommodate the cells, tissues, etc., that are desired to be cultured, and made of any suitable material. The dish 10 has a culture portion 20 having a bottom part 22 and elevated walls 24 surrounding the bottom part. The culture portion 20 is capable of containing the cells and whatever medium they are incubated in. The culture portion is covered by a lid portion 30 (FIG. 2) having a permeable section 40 which is permeable to oxygen and carbon dioxide, but substantially impermeable to water and water vapor. The lid portion 30 is designed so that it can form a water- and gas-tight seal 50 with the culture portion 20 when the lid is placed on the culture portion. This can be achieved by a gasket (such as the o-ring of FIG. 3) or other friction seal (FIG. 1), or by any other means. In one preferred embodiment, the water- and gas-tight seal, and all parts of the culture container and cover, are able to withstand one or more autoclave cycles with no change in functional properties. In other preferred embodiments, the culture container and/or lid portion alone are intended to be completely disposable.

The physical size and configuration of the container covers and culture dishes of the invention can be adapted to any standard size used in the art (e.g., single, multi-well or microtiter formats, screw top or pop-top flasks, etc.), or can be customized for particular vessels. FIGS. 1 and 2 depict a single-well format, such as standard culture plates supplied by companies such as Corning, Falcon, or Nunc. Alternative plate and flask formats are also available from the above suppliers (e.g., multiwell and microtiter plates, numerous culture and media storage flasks). The containers may be any that are suitable for cell culture or media storage, and may be coated with factors to enhance cell adhesion, growth, and/or proliferation (e.g., polylysine). Culture dishes can be configured for specialized uses, for example electrophysiology, drug delivery, or medium exchange, having electrodes in the dish or infusion and outflow ports, for example.

An alternative embodiment of a cover of the invention is shown in FIG. 3, and has a solid support lid portion 60, made of any suitable material, such as plastic (polystyrene, polypropylene, FEP or teflon, for example) or metal. In this embodiment, the permeable section (not shown in FIG.3) is preferably a membrane, which is sufficiently flexible that it can be laid over the top of the lid portion and fastened securely in place with outer band 70. Outer band 70 may be an elastic gasket, o-ring, an adhesive, or any other suitable fastening means. In the embodiment shown in FIG. 3, the band is an o-ring seated within an outer groove 75 in the solid support designed to secure it. The solid support lid portion 60 also has an inner seal 80 that fits into an inner groove 85, and that serves to form a water- and gas-tight seal when the lid portion is placed upon a suitable culture container or vessel. Inner seal 80 may be any material that conforms to the shape of the culture container walls that it touches when engaged or placed upon the container in its operable configuration. Suitable materials are o-rings, elastic gaskets, silastic polymers, etc.

Figure 5:
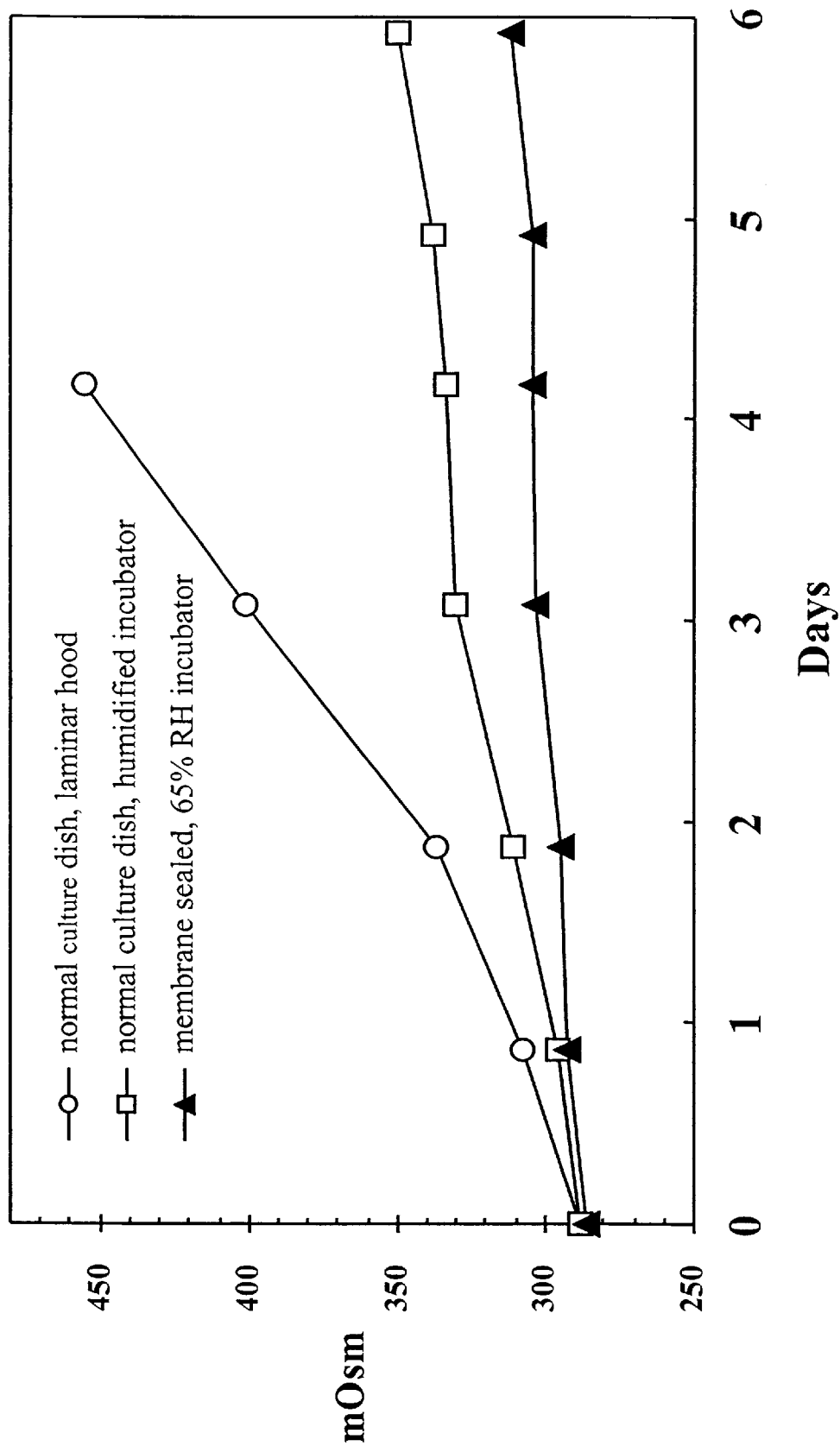
FIG. 5 is a graph showing the rate of equilibration of pH in sealed chambers of the invention as compared to prior art standard culture dishes. Diffusion of carbon dioxide through the FEP membrane is sufficient to allow equilibration of carbonate-buffered media to physiological pH (7.3), but with a somewhat slower time-course than with standard 35 mm culture dishes (falling curves). This lag is beneficial for, e.g., electrophysiology sessions in room air, since it allows recording without a medium change, for at least 30 min, before the upward drift of pH (rising curves) affects cell physiology.

The covers and dishes of the invention permit long term or repeated experiments, such as drug discovery, toxicology, electrophysiology and imaging experiments, to be conducted for months on the same dish of cells. As shown in FIGS. 1, 2 and 5, the dish is completely sealed by a barrier that keeps out pathogens, yet allows equilibration with oxygen and carbon dioxide, which are necessary for cell metabolism and the maintenance of proper pH. This is achieved using a section or membrane on the dish that is permeable to oxygen ($O_2$) and carbon dioxide ($CO_2$), but substantially impermeable to water. Preferably, this permeable section is in the lid or cover of the dish, but may be anywhere on the container. If located elsewhere on the vessel, it is preferably above the ordinary level of any liquid contained in the vessel to maximize exchange of gasses. The cover portion generally has a solid support framework having at least one hole or opening. This opening is covered with the permeable section or membrane. The solid support allows a good contact surface between the cover portion and the vessel walls upon which it rests or engages. Such contact is important to provide a gas-tight and water-tight seal to the interior of the vessel, which prevents evaporation, slows equilibrium disruption when the dish is removed from the incubator, and provides a barrier to contamination. This last point is important in the sense that environmental contamination will not affect the culture. Furthermore, laboratory cultures of potential pathogens under culture (e.g., viruses such as HIV, bacteria such as the causative agent of tuberculosis) are prevented from escaping the dish and contaminating the environment.

A presently preferred membrane is the fluorocarbon polymer, fluorinated ethylene-propylene (FEP Teflon® film, 12.7 $\mu$m thickness, Dupont, Circleville, Ohio). This membrane has the desired features of being completely transparent and optically flat, which allows imaging with, e.g., phase-contrast, fluorescence, and 2-photon microscopy. Clear permeable films such as FEP allow sophisticated imaging without opening and contaminating cells and long term monitoring of individual cultures. FEP membranes are used in oxygen sensors and measuring devices because of their high $O_2$ permeability. However, it is not generally appreciated that they are also permeable to $CO_2$. It is this oxygen and carbon dioxide permeability, as well as its relative impermeability to water and water vapor, that makes it suitable for use in the invention.

The relative impermeability to water of the gas permeable section of the cover or dish of the invention provides a great advantage in terms of standard laboratory practice. A dry incubator full of sealed dishes never has to be cleaned or disinfected. This eliminates one laborious lab task, as well as the problem of where to put the ongoing cultures during cleaning. Cultures can be grown without the use of antibiotics and antimicotics, which are often detrimental to cells even at low levels. Sealed dishes greatly reduce health risks to lab personnel working with dangerous cell lines, cells transfected with viruses, or cultures loaded with radioisotopes or other dangerous chemicals that might be spilled. Furthermore, a dry incubator is much more hospitable to electronic sensors or cell stimulation and recording apparatus that researchers might wish to incorporate with their cultures (Welsh, D. K. et al. (1995), *Neuron* 14: 697–706). Most electronics are much more tolerant of mild (37° C.) heat under dryer conditions, since components are often subjected to significant resistive heating during normal operation. The humid environment found in standard incubators causes electrical shorts, changes in component properties, and destruction of materials commonly found in electronic devices.

Furthermore, evaporation of cell culture medium is a common and underappreciated problem (Maher, M. P. and S. McKinney (1995), *Soc. Neurosci. Abstr.* 21: 229.13). Most cell culture incubators are intended to be maintained at or near 100% relative humidity, to prevent cultures from becoming hyperosmotic. However, the mean relative humidity level is often substantially less, especially in a busy lab in which the incubator is opened several times per day. Even for an open-time of less than one minute, almost the entire volume of warm, humid air rises and escapes out the top of the door opening and is displaced by cooler, dryer room air. Pans of warm water in the bottom of the incubator replenish the humidity relatively slowly, depending on air circulation and the ratio of the surface area of water to the volume of the incubator. Thus, even in a humidified incubator, cultures in standard dishes are subject to evaporation and increasing osmolarity (FIG. 4). This problem is further compounded by the common practice of replacing only half the medium in the dish during feeding. This allows the culture to become more and more hyperosmotic even with repeated feedings with fresh medium, eventually resulting in unhealthy or dead cultures. Data from Maher, supra, show that long-term dissociated cultures of fetal rat hippocampal neurons exhibit extreme sensitivity to pH and osmolarity. Neurons were cultured using 2 mL Neurobasal+B27 medium (Gibco) in 35 mm tissue culture dishes (Falcon), 5% CO2 water-saturated atmosphere at 36° C., 35–50K cells at 500–1000 cells/mm2, fed once weekly by replacing half the medium. Opening the incubator several times daily for observation and feeding caused the interior CO2 concentration and humidity to vary, with a net loss of water. Under normal operating conditions, medium in the dishes in the incubator lost 75 $\mu$L/day of water and increased in osmolarity by 8 mOs/kg per day. Over the course of 2 weeks in culture with a standard feeding schedule, the osmolarity rose from its ideal value of 220 mOs/kg to 280 mOs/kg, and cell survival fell to zero. Cells began dying after 2 days when the medium was maintained at 270 mOs/kg, and all cells were dead after 4 days at this high osmolarity. Exposing covered 35 mm tissue culture dishes of $CO_2$-based media to air at 23° C. caused the pH to rise to 7.7 in 10 minutes. Exposure to pH in excess of 7.7 for more than a few minutes also killed the neurons. These effects are not immediately apparent; cell morphology may appear good for a day or more after exposure to high pH.

Another study of one incubator showed it took 25 minutes to reach 90% of the original relative humidity value (95% RH) after one 30-second incubator door opening (data not shown). The pan was 0.10 $m^2$, and the incubator volume was 153 L.

By growing cultures in sealed dishes, one does not have to worry about trying to rapidly remove a dish and close the door before all the humid air pours out. The osmolarity in the dishes remains relatively constant regardless of the relative humidity in the incubator (FIG. 4). Without fear of humidity fluctuations or infection from the influx of room air, one is free to transfer cultures into and out of the incubator at a more leisurely and careful pace.

The invention is described more fully in the following Examples, which are presented for illustrative purposes only and are not intended to limit the scope of the invention.

EXAMPLE 1

In one embodiment, a re-usable lid portion is used on a commercially-available electrophysiology dish (e.g., MEA60 made by Multichannel Systems, Reutlingen, Germany (www.multichannelsystems.com) or the Panasonic Multi-Electrode Dish (http://www.med64.com/)). Re-usable culture dish lids (FIG. 3) consisted of a Teflon® cylinder fitted with two rubber o-rings (EP75, Real Seal, Escondido, Calif.). The inner o-ring seals the lid to the culture dish, and the outer o-ring holds the FEP membrane on. For control cultures that do not need multi-electrode arrays, culture dishes were constructed by gluing glass rings to microscope slides with a silastic adhesive (MDX4-4210, Dow Corning). Fluorocarbon polymers are useful not only for their selective permeability to gases, but also for their chemical inertness and temperature stability. FEP, and the other materials mentioned, can be repeatedly sterilized in a standard autoclave with no change in their physical properties. For electrophysiology, a ground lead consisting of a fine platinum wire is inserted through a pinhole in the Teflon cylinder, and glued in place with silastic adhesive.

The sealed culture dishes are substantially impermeable to water, which allows cultures to be grown in a dry incubator (e.g., ambient humidity level), that does not tend to harbor pathogens. We compared increases in osmolarity of medium due to evaporation in sealed dishes in a dry incubator to those in standard (unsealed) polystyrene 35 mm culture dishes (Corning; whose lids have an air gap built in) in a humidified incubator, and in a laminar-flow hood (FIG. 4).

EXAMPLE 2

Equilibration Rates of $CO_2$ Across FEP Membrane

In order to study $CO_2$ equilibration rates in dishes sealed with FEP membrane, $CO_2$-buffered medium was left out in ambient air overnight, until its pH leveled off at about 8.5. It was then placed in standard culture dishes in a standard, humidified 5% $CO_2$ incubator, or in sealed dishes in a dry, 5% $CO_2$ incubator. As can be seen in FIG. 5, the equilibration rate is significantly slower in sealed dishes than in unsealed Corning culture dishes. The rate of equilibration is acceptably rapid for general culture purposes, and offers the advantage that dishes removed from an incubator for an experiment do not experience large pH shifts over the time period of the experiment. This reduces or eliminates one undesirable variable from the experiment. For example, the slower pH equilibration of FEP-sealed dishes is an advantage for multi-electrode array recording. Recordings can be made from sealed dishes at ambient $CO_2$ levels for several hours without experiencing detrimental pH drift in $CO_2$-buffered media. Thus, no medium change is necessary for recording, reducing the chance of infection, and eliminating the electrophysiological transients that ensue after a medium change (Gross, G. W. and J. Kowalski (1991), In: *Neural Networks: Concepts applications and implementations*, P. Antognetti and E. B Milutinovic, eds., NJ, Prentice-Hall, 4: 47–110). This is the main advantage over continuous-perfusion sealed culture chambers developed by others ( Gross, G. W. and F. U. Schwalm (1994), *J. Neurosci Meth* 52: 73–85; Freyberg, M. A. and P. Friedl (1998), *Cytotechnology* 26: 49–58).

Data have been obtained in primary rat cortical neural cell cultures that are still spontaneously electrically active and healthy after over seven months of incubation in sealed multielectrode dishes. These dishes are only opened in a sterile laminar flow hood, to change the medium weekly.

Thus, the culture covers, vessels, and methods of the invention described herein provide numerous benefits for cell culture, including:

Greatly reducing or eliminating the occurrence of infected or cross-contaminated cultures.

need for laborious incubator cleaning and disinfection.

the potential hazard of exposure to pathogens that grow in humid incubators.

Reducing risk to lab personnel from spills or aerosols of dangerous media components and cell lines.

Allowing repeated observation of cultures, for cell-counting, etc.

Enhancing visibility into the incubator, since there is no condensation on the glass door.

Allowing electronic sensors to be placed in the incubator with the cells without fear of moisture damage to the electronics.

Allowing imaging and electrophysiological recording without changing the medium or experiencing rapid pH fluctuations.

The preceding description has been presented with references to presently preferred embodiments of the invention. Persons skilled in the art and technology to which this invention pertains will appreciate that alterations and changes in the described structures and methods can be practiced without meaningfully departing from the principle, spirit and scope of this invention.

Accordingly, the foregoing description should not be read as pertaining only to the precise structures and methods described and shown in the accompanying drawings, but rather should be read as consistent with and as support for the following claims, which are to have their fullest and fairest scope.

What is claimed is:

1. A gas permeable cover for a container, the cover comprising:

a solid support sized to fit the opening of the container to be covered, the support having at least one hole;

a permeable section which covers the at least one hole, the permeable section being sufficiently permeable to oxygen and carbon dioxide such that a physiologically acceptable pH is sustained within the container, sufficiently impermeable to water vapor such that a relatively constant osmolarity is sustained within the container without intervention by a user, and substantially impermeable to liquid water; and a seal portion which forms a water-tight and gas-tight seal between the cover and the container when the cover is placed upon the container as configured for use.

2. The gas permeable cover of claim 1 wherein the permeable section passes water and water vapor at a rate of less than about 5 mol/m$^2$·day at 25° C. and 1 atmosphere.

3. The gas permeable cover of claim 1 wherein the permeable section passes water and water vapor at a rate of less than about 3 mol/m$^2$·day at 25° C. and 1 atmosphere.

4. The gas permeable cover of claim 1 wherein the permeable section passes water and water vapor at a rate of less than about 2 mol/m$^2$·day at 25° C. and 1 atmosphere.

5. The gas permeable cover of claim 1 wherein the permeable section passes water and water vapor at a rate of less than about 1 mol/m$^2$·day at 25° C. and 1 atmosphere.

6. The gas permeable cover of claim 1 wherein the permeable section passes oxygen gas at a rate of greater than about 0.25 mol/m$^2$·day at 25° C. and 1 atmosphere.

7. The gas permeable cover of claim 1 wherein the permeable section passes oxygen gas at a rate of greater than about 0.5 mol/m$^2$·day at 25° C. and 1 atmosphere.

8. The gas permeable cover of claim 1 wherein the permeable section passes oxygen gas at a rate of greater than about 0.8 mol/m$^2$·day at 20° C. and 1 atmosphere.

9. The gas permeable cover of claim 1 wherein the permeable section passes carbon dioxide gas at a rate of greater than about 0.5 mol/m$^2$·day at 25° C. and 1 atmosphere.

10. The gas permeable cover of claim 1 wherein the permeable section passes carbon dioxide gas at a rate of greater than about 1.0 mol/m$^2$·day at 20° C. and 1 atmosphere.

11. The gas permeable cover of claim 1 wherein the permeable section passes carbon dioxide gas at a rate of greater than about 1.5 mol/m$^2$·day at 20° C. and 1 atmosphere.

12. The cover of claim 1 wherein the permeable section is fixed onto the solid support.

13. The cover of claim 1 wherein the permeable section is comprised of a fluorocarbon polymer.

14. The cover of claim 1 wherein the permeable section is comprised of fluorinated ethylene-propylene film.

15. The cover of claim 1 wherein the permeable section is impermeable to viruses, mold, bacteria, and fungi.

16. The cover of claim 1 wherein the cover and the permeable section are substantially made of the same material.

17. A culture dish for culture of viable cells comprising:

a culture portion having a bottom part and elevated walls surrounding the bottom part, the culture portion being capable of containing the cells, a lid portion having a permeable section, the permeable section being sufficiently permeable to oxygen and carbon dioxide such that a physiologically acceptable pH is sustained within the container, sufficiently impermeable to water vapor such that a relatively constant osmolarity is sustained within the container without intervention by a user, and substantially impermeable to liquid water; and a seal portion which forms a water-tight and gas-tight seal between the lid portion and the walls when the cover is placed upon the walls as configured for use.

18. The dish of claim 17 wherein the water-tight and gas-tight seal is created by the weight of the lid portion against the walls.

19. The dish of claim 17 wherein the water-tight and gas-tight seal is created by a friction seal between the lid portion and the walls.

20. The dish of claim 19 wherein the friction seal is created by a gasket.

21. The dish of claim 17 wherein the lid portion further comprises a top part and walls surrounding the top part.

22. The dish of claim 19 wherein the lid portion further comprises a top part and walls surrounding the top part which taper outward, and wherein the friction seal is created by contact between the tapered walls of the top part and the walls of the bottom part.

23. The dish of claim 17 wherein the permeable section is fixedly attached to the lid portion.

24. The dish of claim 17 wherein the permeable section is passes water and water vapor at a rate of less than about 5 mol/m$^2$·day at 20° C. and 1 atmosphere.

25. The dish of claim 17 wherein the permeable section is passes water and water vapor at a rate of less than about 3 mol/m$^2$·day at 20° C. and 1 atmosphere.

26. The dish of claim 17 wherein the permeable section is passes water and water vapor at a rate of less than about 1 mol/m$^2$·day at 25° C. and 1 atmosphere.

27. The dish of claim 17 wherein the permeable section is passes oxygen gas at a rate of greater than about 0.5 mol/m$^2$·day at 20° C. and 1 atmosphere.

28. The dish of claim 17 wherein the permeable section is passes carbon dioxide gas at a rate of greater than about 1.0 mol/m$^2$·day at 20° C. and 1 atmosphere.

29. The dish of claim 17 further comprising at least one electrode.

30. The dish of claim 17 further comprising at least one of an infusion and outflow port.

31. A method of culturing cells comprising:

providing cells and culture medium in a culture vessel, wherein the culture vessel comprises a culture container portion capable of containing the cells, a cover portion comprising a solid support sized to fit the opening of the container and having at least one hole, a permeable section which covers the at least one hole, the permeable section being sufficiently permeable to oxygen and carbon dioxide such that a physiologically acceptable pH is sustained within the container, sufficiently impermeable to water vapor such that a relatively constant osmolarity is sustained within the container, and substantially impermeable to liquid water, and a seal portion which forms a water-tight and gas-tight seal between the cover and the container when the cover is placed upon the container as configured for use; and incubating the cells under conditions physiologically compatible with cell viability without external regulation of the flow of water vapor by a user.

32. The method of claim 31 further comprising periodically changing a sufficient amount of the culture medium such that the cells have food and toxic levels of waste are removed.

33. The method of claim 31 wherein the cells are incubated in a non-humidified incubator.

34. The method of claim 31 wherein the relative humidity of the incubator is less than about 85%.

35. The method of claim 34 wherein the relative humidity of the incubator is less than about 65%.

36. The method of claim 34 wherein the relative humidity of the incubator is less than about 50%.

37. The method of claim 34 wherein the relative humidity of the incubator is less than about 30%.

38. The method of claim 34 wherein the relative humidity of the incubator is less than about 20%.

39. A gas permeable cover for a container, the cover comprising:

a solid support sized to fit the opening of the container to be covered, the support having at least one hole;

a permeable section which covers the at least one hole, the permeable section being sufficiently permeable to oxygen and carbon dioxide such that a physiologically acceptable pH is sustained within the container, sufficiently impermeable to water vapor such that a relatively constant osmolarity is sustained within the container without intervention by a user, and substantially impermeable to liquid water; and a seal portion which forms a water-tight and gas-tight seal between the cover and the container, wherein the water-tight and gas-tight seal is created by the weight of the cover against the container when the cover is placed upon the container as configured for use.

40. A culture dish for culture of viable cells comprising:

a culture portion having a bottom part and elevated walls surrounding the bottom part, the culture portion being capable of containing the cells, a lid portion having a permeable section, the permeable section being sufficiently permeable to oxygen and carbon dioxide such that a physiologically acceptable pH is sustained within the container, sufficiently impermeable to water vapor such that a relatively constant osmolarity is sustained within the container without intervention by a user, and substantially impermeable to liquid water; and a seal portion which forms a water-tight and gas-tight seal between the lid portion and the walls, wherein the water-tight and gas-tight seal is created by the weight of the lid portion against the walls when the cover is placed upon the walls as configured for use.

41. A method of culturing cells comprising:

providing cells and culture medium in a culture vessel, wherein the culture vessel comprises
   a culture container portion capable of containing the cells, a cover portion comprising
      a solid support sized to fit the opening of the container and having at least one hole,
      a permeable section which covers the at least one hole, the permeable section being sufficiently permeable to oxygen and carbon dioxide such that a physiologically acceptable pH is sustained within the container, sufficiently impermeable to water vapor such that a relatively constant osmolarity is sustained within the container, and substantially impermeable to liquid water, and
      a seal portion which forms a water-tight and gas-tight seal between the cover and the container when the cover is placed upon the container as configured for use;

placing the culture vessel in a non-humidified incubator; and incubating the cells under conditions physiologically compatible with cell viability without external regulation of the flow of water vapor by a user.

* * * * *